United States Patent
Palmer et al.

(10) Patent No.: US 11,090,626 B2
(45) Date of Patent: Aug. 17, 2021

(54) NANOPARTICLE PRODUCTION

(71) Applicants: MIDATECH LTD., Abingdon (GB); MIDATECH PHARMA (WALES) LIMITED, South Glamorgan (GB)

(72) Inventors: Daniel Palmer, Cardiff (GB); Rhian Groves, Cardiff (GB); Paul Seaman, Cardiff (GB); Victoria Cavalier-Hirth, Cardiff (GB); Alessandro Pace, Abingdon (GB)

( * ) Notice: Subject to any disclaimer, the term of this patent is extended or adjusted under 35 U.S.C. 154(b) by 0 days.

(21) Appl. No.: 16/077,703

(22) PCT Filed: Feb. 22, 2017

(86) PCT No.: PCT/EP2017/054096
§ 371 (c)(1),
(2) Date: Aug. 13, 2018

(87) PCT Pub. No.: WO2017/144551
PCT Pub. Date: Aug. 31, 2017

(65) Prior Publication Data
US 2019/0039039 A1    Feb. 7, 2019

(30) Foreign Application Priority Data
Feb. 26, 2016 (GB) .................................. 1603358

(51) Int. Cl.
*B01J 13/04* (2006.01)
*B01J 13/02* (2006.01)
*A61K 47/69* (2017.01)

(52) U.S. Cl.
CPC ........... *B01J 13/04* (2013.01); *A61K 47/6923* (2017.08); *A61K 47/6929* (2017.08); *B01J 13/02* (2013.01)

(58) Field of Classification Search
CPC . A61K 47/6929; A61K 47/6923; B01J 13/04; B01J 13/02
See application file for complete search history.

(56) References Cited

U.S. PATENT DOCUMENTS

| | | | |
|---|---|---|---|
| 2012/0171291 A1* | 7/2012 | Rademacher | A61K 47/6923 424/490 |
| 2013/0087020 A1* | 4/2013 | Brutchey | B22F 9/24 75/370 |
| 2014/0220135 A1 | 8/2014 | Rademacher | |

FOREIGN PATENT DOCUMENTS

| | | |
|---|---|---|
| CN | 103241761 | 8/2013 |
| CN | 103464744 | 12/2013 |
| CN | 104028778 | 9/2014 |
| WO | 2010/052503 | 5/2010 |
| WO | 2011/154711 | 12/2011 |
| WO | 2011/156711 | 12/2011 |
| WO | 2012042273 | 4/2012 |
| WO | 2012/170828 | 12/2012 |
| WO | 2014/122444 | 8/2014 |
| WO | 2016/075211 | 5/2016 |

OTHER PUBLICATIONS

Nightingale et al., "Controlled multistep synthesis in a three-phase droplet reactor," May 6, 2014, Nature Communications.*
Schollbach et al., "Gold nanoparticles decorated with oligo(ethylene glycol) thiols: Surface charges and interactions with proteins in solution," Journal of Colloid and Interface Science 426 (2014) 31-38.*
Tai et al., "Preparation of Silver Nanoparticles Using a Spinning Disc Reactor in Continuous Mode," Ind. Eng. Chem. Res. 2009, 48, 10104-10109.*
Ulmke et al., "The Piezoelectric Droplet Generator—A Versatile Tool for Dispensing Applications and Calibration of Particle Sizing Instruments," International euspen Conference, vol. 2, Shaker Verlag, Aachen 1999, 299-293.*

* cited by examiner

*Primary Examiner* — Jared Barsky
(74) *Attorney, Agent, or Firm* — Rudy J. Ng; Bozicevic, Field & Francis LLP (57) ABSTRACT

The present invention provides a process for producing nanoparticles, comprising: providing a first liquid comprising a metal salt and at least one species of ligand having a functional group capable of binding to a metal surface, providing a second liquid comprising a reducing agent; providing at least one liquid droplet generator operable to generate liquid droplets, causing the at least one liquid droplet generator to form liquid droplets of the first liquid, passing the liquid droplets through a gas to contact the second liquid so as to cause the metal salt and the at least one species of ligand to come into contact with the reducing agent, thereby causing self-assembly of nanoparticles, said nanoparticles having a core of said metal and a corona comprising a plurality of said ligands covalently bound to the core. Also provided are nanoparticles produced by the process of the invention and use of such nanoparticles in medicine.

15 Claims, 6 Drawing Sheets

NANOPARTICLE PRODUCTION

FIELD OF THE INVENTION

The present invention relates to processes for the production of nanoparticles, particularly nanoparticles having a metal or semiconductor core, which core is covalently bound by a plurality of ligands. The nanoparticles may have one or more payloads covalently or non-covalently bound thereto, for example acting as pharmaceutical carriers.

BACKGROUND TO THE INVENTION

The present invention is directed at methods for the production of nanoparticles. Nanoparticles for use in medical and diagnostic applications, and methods for their production are known. WO 02/32404 describes the synthesis and characterisation of gold nanoparticles functionalised with thiol derivatised carbohydrate ligands (glyconanoparticles). A solution of the ligands (in disulphide form) in methanol was added to a solution of tetrachloroauric acid in water. Sodium borohydride in water was added in small portions with rapid stirring to the vessel containing the ligands and gold salt. A black suspension was formed as a result of nanoparticle self-assembly.

WO 2016/075211 A1 describes sustained release encapsulated nanoparticles and methods for their production.

WO 2014/122444 A1 describes permeation enhanced active-carrying nanoparticles for use in medicine and methods for production of such nanoparticles.

WO 2011/156711 A1 describes a therapeutic film delivery system which includes nanoparticles having actives bound to or associated with the nanoparticles, as well as methods for forming the nanoparticles and film comprising the nanoparticles.

WO 2010/052503 A1 describes the use of metal core nanoparticles for imaging a tumour in a mammal using electrical impedance tomography. Also described are methods for forming the nanoparticles.

WO 2012/170828 A1 describes nanoparticles having a core and a corona of ligands covalently linked to the core, wherein differing species of peptides are bound to the nanoparticles and incorporated into various dosage forms, including films. Methods for producing the nanoparticles, binding peptides thereto and incorporating the nanoparticles into film are also described.

The further development of glycated gold nanoparticles, for example in medical and diagnostic applications, has created the need for scaled-up synthesis methods that provide for controlled production of monodisperse nanoparticles in quantities that exceed that of traditional laboratory synthesis techniques. A particular problem with the aforementioned synthesis method (e.g. described in WO 02/32404) is that uniformity of the resultant nanoparticle properties (including size) depends in large part on achieving near instantaneous mixing of the added sodium borohydride with the gold salt and thiol-derivatised ligands. Moreover, the sodium borohydride is a source of potentially flammable hydrogen gas, which therefore necessitates carefully controlled conditions, especially for larger-scale reaction methods. Controlling foaming caused by hydrogen gas production within the reactor is a problem. At larger scale, significant foaming is seen upon addition of $NaBH_4$, and this sometimes necessitates the addition of an anti-foaming agent. It would be desirable to minimise the need for, or even avoid, the addition of an anti-foaming agent during nanoparticle synthesis.

There remains an unmet need for methods of producing metal-containing nanoparticles of uniform properties at scale in a controlled fashion and without undesirable foaming. The present invention addresses this and other needs.

BRIEF DESCRIPTION OF THE INVENTION

Broadly, the present invention relates to nanoparticle production methods in which a solution comprising nanoparticle reactants (e.g. metal salts and derivatised ligands) are added dropwise to a solution containing a reducing agent (e.g. sodium borohydride). The relatively small size of the droplets containing the nanoparticle reactants tends to ensure rapid mixing and consequently increasingly uniform properties of the nanoparticles produced (such as tighter size distribution). The solution containing the nanoparticle reactants may conveniently be ejected as droplets from a droplet generator to pass through a gas into the solution containing the reducing agent. The solution containing the reducing agent may be provided in the form of a continuously-stirred pool of liquid in a vessel or in the form of a liquid stream (e.g. in a channel or as a jet of the liquid passing through a gas). The present inventors have surprisingly found that nanoparticles produced in this way exhibit good uniformity. Moreover, this method of producing nanoparticles is more amenable to scale-up, not least because constraints imposed by previously known methods of production (e.g. rate of mixing of the reducing agent and changes in reducing agent concentration over time) are largely avoided by the production method of the present invention.

Accordingly, in a first aspect the present invention provides a process for producing nanoparticles, comprising:
  providing a first liquid comprising a core-forming material (typically a metal salt) and at least one species of ligands having a functional group capable of binding to a metal surface (e.g. a thiol-containing polar organic compound),
  providing a second liquid comprising a reducing agent (e.g. a solution containing sodium borohydride);
  providing at least one liquid droplet generator operable to generate liquid droplets,
  causing the at least one liquid droplet generator to form liquid droplets of the first liquid,
  passing the liquid droplets through a gas to contact the second liquid so as to cause the core-forming material (e.g. the metal salt) and the at least one species of ligand to come into contact with the reducing agent, thereby causing self-assembly of nanoparticles, said nanoparticles having a core (e.g. of metal reduced from said metal salt) and a corona comprising a plurality of said ligands covalently bound to the core.

In some cases, the metal salt comprises a salt of Au, Ag, Cu, Pt, Pd, Fe, Co, Gd, Eu, and/or Zn. In particular, the metal salt may be $HAuCl_4$. The concentration of metal salt (e.g. $HAuCl_4$) in the first liquid may be, for example, in the range 0.1-100 mg/mL, e.g. 1-30 mg/mL.

Nanoparticles having a semiconductor (quantum dot) core, such as ZnS, CdS and CdSe, have been described previously (de la Fuente and Penadés, *Tetrahedron: Asymmetry*, 2005, Vol. 16, pp. 387-391). It is contemplated herein that the first liquid may comprise, for example, cadmium nitrate and disulphide-derivatized carbohydrates and the second liquid may comprise sodium sulphide, thereby forming a glycated quantum dot having a core of CdS.

In accordance with the first aspect of the present invention, the at least one species of ligand may comprise a sulphide, a thiol or may be provided as ligand dimers linked by a disulphide bridge.

The concentration of the ligands in the first liquid may be, for example, in molar excess relative to the concentration of metal salt. In some cases, the ligands are present in the first liquid at a ratio to the metal salt of between 1.1:1 to 5:1, e.g. 1.5:1, 2:1, 2.5:1, 3:1, 3.5:1, 4:1, 4.5:1 or 5:1. In certain cases, the ligands are present in the first liquid at 3 equivalents of the metal salt (e.g. Glucose-C2 disulphide:$Au^{3+}$ at 3:1 mole ratio).

In some cases the at least one species of ligand comprises one or more of a carbohydrate moiety, an alkyl chain, a glycol chain and glutathione. Glutathione naturally possesses a thiol in the form of the cysteine amino acid, which facilitates covalent linkage to the surface of the metal (e.g. gold) core. The ligand may, for example, take the form of a conjugate, such as thiol-$C_{2-12}$ alkyl-saccharide.

In some cases the carbohydrate moiety is a monosaccharide (e.g. five carbon monosaccharide such as ribose, or a six carbon monosaccharide such as glucose), a disaccharide (e.g. lactose or maltose), an oligosaccharide or a polysaccharide. In particular cases, the carbohydrate moiety comprises glucose, galactose, glucosamine, N-acetylglucosamine, mannose, fucose and/or lactose, or a glycoside thereof.

In some cases, the at least one species of ligand comprises an oligo ethylene glycol or a polyethylene glycol. In particular cases, the at least one species of ligand may comprise a hexaethylene glycol. In certain cases, the at least one species of ligand comprises 1-amino-17-mercapto-3,6,9,12,15-pentaoxa-heptadecanol. In certain cases, the ligand may comprise a negatively charged end group or an end group capable of having negative charge at physiological pH. The dilution ligand may have a carboxylic acid end group. In particular, the dilution ligand may comprise SH-PEG-COOH. In certain cases, the at least one dilution ligand comprises: HS—$(OCH_2CH_2)_m$—COOH, where m is between 2 and 30, optionally between 6 and 10. In certain cases m may be 2, 3, 4, 5, 6, 7, 8, 9, 10, 11, 12, 13, 14, 15, 16, 17, 18, 19 or 20.

In some cases, the at least one species of ligand comprises a therapeutic and/or bioaffecting agent. An exemplary class of therapeutic agent is an anti-cancer agent, such as a cytotoxic compound, an anti-proliferative agent or an anti-angiogenic agent. In particular, the at least one species of ligand may comprise a compound selected from the group consisting of: doxorubicin, irinotecan, platinum (II), platinum (IV), temozolomide, chlorotoxin, carmustine, camptothecin, docetaxel, sorafenib, maytansine, a maytansinoid (e.g. maytansinoid DM1 or maytansinoid DM4), monomethyl auristatin E (MMAE) and a histone deacetylase (HDAC) inhibitor (e.g. panobinostat).

In certain cases, the at least one species of ligand is selected from:

In some cases, the therapeutic agent or bioaffecting agent comprises a peptide, a polypeptide and/or a nucleic acid (e.g. DNA or RNA, such as siRNA, miRNA or shRNA). The peptide or polypeptide may, in some cases have one or more post-translational modifications, for example it may be glycosylated. The therapeutic agent or bioaffecting agent (for example, the peptide or polypeptide) may comprise or present one or more epitopes. In particular, the agent, for example the peptide or polypeptide, may be an antigen. In certain cases, the antigen may be an auto-antigen implicated in a human autoimmune disease, for example an auto-antigen peptide. Numerous examples of auto-antigen peptide are known. In certain cases, the auto-antigen peptide may be an auto-antigen implicated in type 1 diabetes mellitus (e.g. proinsulin, glutamic acid decarboxylase (GAD), IA2, islet cell antigens, chromogranin A, or a fragment of any one of the aforementioned). Alternatively, the peptide or polypeptide may be a synthetic or hybrid sequence derived from one or more naturally-occurring peptide sequences.

In some cases, the at least one species of ligand comprises a detectable label, such as a fluorescent label or an opto-acoustic dye.

In some cases, the at least one species of ligand comprises a targeting moiety. The targeting moiety selectively targets, binds to, or is taken up by, a particular receptor, cell type, tissue, tumour or organ. The targeting moiety may facilitate targeting of the resultant nanoparticles to certain sites of interest, e.g., tumour or diseased tissue sites, organ types or particular cell types.

In certain cases, the targeting moiety may be selected from the group consisting of: folic acid, lactose, albumin, glutamine, a peptide, a polypeptide, a ligand that binds a cell surface receptor (e.g. an EGFR ligand such as Gefitinib), an antibody, an antibody fragment (e.g. Fab, scFv and the like), and an aptamer. In some cases the antibody or fragment thereof, binds selectively to a tumour associated antigen.

In some cases, the at least one species of ligand comprises at least 2, 3, 4 or at least 5 different species of ligand. In particular, the different species of ligand may include 2, 3, 4, 5 or more of the different ligands discussed herein. The different species of ligand may be provided in the first liquid at a particular ratio (e.g. between 1:40 and 40:1). It is contemplated that the ratio of ligand species in the first liquid will to a large extent be reflected in the ratio of covalently bound ligands that make up the corona of the resulting nanoparticles. The ratio of covalently bound ligands can be determined after synthesis using a variety of well-known techniques. For example, the presence of and relative proportions of ligands may be determined using NMR.

In particular cases, the at least 2 species of ligand comprise:
  (i) 2'-thioethyl-α-D-galactopyranoside and
  (ii) 1-amino-17-mercapto-3,6,9,12,15,-pentaoxa-heptadecanol.

The two species of ligand (i) and (ii) may be provided in the first liquid at a ratio in the range 10:90 to 90:10, e.g., 40:60 to 60:40.

In some cases the average diameter of the core of the nanoparticles formed by the process of the present invention is in the range 1 nm to 5 nm. The diameter of the nanoparticle including its ligands may in some cases be in the range 2 nm to 50 nm, or 3 nm to 30 nm, or 4 nm to 20 nm, or 5 nm to 15 nm.

In some cases, said first liquid further comprises dimethyl sulphoxide (DMSO). DMSO is well-known as a solubility aid and has been found to assist droplet generation, e.g., from a piezoelectric droplet generator. In some cases, said first liquid further comprises an alcohol, e.g. methanol, and/or water.

In some cases in accordance with the first aspect of the present invention, said reducing agent may be selected from the group consisting of: $NaBH_4$, hydrazine hydrate, $NaBH_3CN$ (cyanoborohydride) and DIBAL (diisobutyl aluminium hydride). In certain cases the reducing agent may be $NaBH_4$. The concentration of the reducing agent (e.g. $NaBH_4$) in the second liquid may be, for example 0.01 to 0.1 M, e.g. 0.05 M In some cases in accordance with the first aspect of the present invention, the at least one liquid droplet generator comprises a piezoelectric component. In certain embodiments of the process the droplet ejection process makes use of the piezoelectric effect, whereby a piezo crystal undergoes distortion when an electric pulse is applied. This distortion results in a pressure pulse, forcing a droplet to be ejected from a nozzle and also creating negative pressure to pull in more fluid once the droplet has been ejected. Many off-the-shelf devices make use of this principle to generate droplets, particularly within the printing industry.

In some cases, the droplet generator or generators operate in drop-on-demand mode. In some cases, a signal generator supplies an electric field to the piezoelectric component.

In some cases, the at least one liquid droplet generator comprises a plurality of droplet generator outlets and wherein the droplet generator outlets are in a line or an array. In some cases, the at least one liquid droplet generator is in the form of an inkjet print-head.

The second liquid may be provided in any configuration that permits the droplets of the first liquid, after being dispensed from the liquid droplet generator(s) and passing through a gas, to enter or make contact with a surface of the second liquid. In certain cases, the second liquid may be provided in an open-topped vessel, a thin film, or a spinning disc reactor. In certain cases, the vessel may be a stirred flask or bath. Stirring facilitates distribution of the reducing agent and helps to maintain a uniform concentration of the reducing agent in the second liquid. This helps to prevent local areas of lowered reducing agent concentration at the site of entry of the liquid droplets of the first liquid.

In other cases, the second liquid may be provided as at least one stream in one or more channels.

In still further cases, the second liquid may be provided as a jet passing through a gas (e.g. air). In particular, the jet of second liquid is generated by providing a continuous, pulseless flow of said second liquid and passing said flow of second liquid through a nozzle which causes a reduction in the cross-sectional area available for flow and thereby increases the flow velocity of the second liquid, said nozzle terminating in an orifice from which the jet of second liquid emerges. In some cases, the jet of second liquid is not in contact with any wall or channel for at least part of its length. In particular embodiments, the part of the length of the jet not in contact with any wall or channel comprises a contact zone, said contact zone being the zone of the jet in which said liquid droplets make contact with said jet.

A particular advantage of providing the second liquid as a flow in a channel or as a jet is that the concentration of the reducing agent can readily be maintained at a constant level. When the nanoparticle reactants (metal salt and ligands) are added to a vessel containing reducing agent at a particular concentration, the reducing agent concentration will deplete with time as more and more droplets of the first liquid are added. This will not be the case where the second liquid is provided as a flow or jet because the concentration of reducing agent in the second liquid at the site of initial contact of the droplets of the first liquid will be constant over time. This in turn helps to ensure consistency of properties (e.g. size) within a production batch. In some cases, the jet approach ensures constant reaction conditions with no meaningful concentration depletions in either the first or second liquids.

In some cases, the liquid droplets of said first liquid pass through gas (e.g. air) for a distance of 1 to 100 mm, optionally 2 to 10 mm before contacting said second liquid.

In some cases, the flow or jet of second liquid flows substantially perpendicular to the direction of droplet ejection and substantially parallel to the longitudinal axis of the plurality of liquid droplet generator outlets.

In some cases, the at least one liquid droplet generator is positioned above the second liquid and said liquid droplets are ejected downwards towards the second liquid with an initial velocity and/or under the assistance of gravity.

In some cases, a plurality of liquid droplets of said first liquid are dispensed from respective liquid droplet generator outlets substantially simultaneously and the liquid droplets pass through gas (e.g. air) in parallel before contacting said second liquid.

In some cases, the number of liquid droplet generator outlets is in the range 5 to 2500, optionally 256, 512 or 1024.

In some cases, the frequency of liquid droplet generation is in the range 0.1 to 100 kHz, optionally 1 to 10 kHz, wherein the stated frequency is per droplet generator outlet (e.g. per nozzle). The total frequency in aggregate across all nozzles may be considerably higher, for example, in the MHz range (see, e.g., Example 1 herein describing aggregate frequency of 2.05 MHz).

In some cases, the liquid droplets have an individual droplet volume in the range 1 to 100 pL, optionally 20 to 60 pL.

In some cases in accordance with the first aspect of the present invention, the process is for producing meta-stable nanoparticles. In this context, a "meta-stable" or "meta-stable" nanoparticle is a nanoparticle having one or more (e.g. 2, 3, 4, 5, 6, 7, 8, 9, 10 or more) surface exposed atoms (e.g. gold atoms) of the nanoparticle core that is or are not capped with a ligand. The percentage of surface exposed atoms of the nanoparticle core that are not covalently bound to a ligand (i.e. are uncapped) may in some cases by at least 10%, 20%, 30%, 40% or 50%. In certain embodiments, the ratio of ligands to core-forming material (e.g. metal salt) may be selected so that the nanoparticles formed are not fully capped or passivated with ligands.

In some cases in accordance with the first aspect of the present invention, the process further comprises a step of adding further ligands to a solution comprising the nanoparticles. It has been found that the nanoparticles can be initially formed in a meta-stable state, if desired. Alternatively, a greater excess of ligands can be added—in the synthesis or post-synthesis—to produce fully stable nanoparticles. Without wishing to be bound by any particular theory, the present inventors believe that the nanoparticles initially formed in a meta-stable state have a core which is not fully passivated (i.e. capped) with ligands. Over time the meta-stable nanoparticles may be subject to ligand displacement reactions and/or core coalescence, which alter properties such as the size of the nanoparticles. In particular, gold atoms may be displaced if they are exposed, i.e. they will be available to merge with other exposed gold surfaces, and these would reorganise to form larger nanoparticles. As demonstrated in the Examples, addition of excess unreacted ligands (e.g. 3× molar excess of glucose C2 disulphide) 20 minutes after ejection of the first liquid from liquid droplet generators into the second liquid was complete, and subsequent stirring of the mixture, resulted in fully stable nanoparticles having a narrow size distribution and near complete absence of a plasmon resonance band.

In some cases, the further added ligands are the same as the at least one species of ligand in the first liquid. In this way subsequent ligand binding to uncapped core surface atoms or competitive displacement of existing ligands tends to result in addition of "more of the same" or like-for-like ligand replacement, and thereby stabilises the nanoparticle make-up (shifting from meta-stable to fully stable).

In some cases, the further added ligands are different from the at least one species of ligand in the first liquid. In this way subsequent ligand binding to uncapped core surface atoms or competitive displacement of existing ligands tends to result in addition of different ligands thereby producing a nanoparticle having a mixed corona. A particular advantage envisaged for the addition of ligands that are different from the at least one species of ligand in the first liquid is the ability to bind ligands to the nanoparticle that would not be stable in contact with the reducing agent. For example, the process may employ a first ligand "A" in the first liquid to form initially a meta-stable nanoparticle having a corona of ligands "A". To the solution containing these nanoparticles an amount, such as an excess, of a second ligand "B" may be added. The second ligand may then populate uncapped sites on the surface of the core of the nanoparticle and/or may displace a portion of the ligands "A". The result would then be a nanoparticle having a mixed corona of ligands "A" and "B". In this example, "B" need not be stable in the presence of the reducing agent and/or need not be provided in the first liquid. This approach therefore frees up the possible choice of "B" to include ligands that are unsuited to the initial synthesis conditions (e.g. exposure to the reducing agent). One particular example of this approach is in the synthesis of nanoparticles having at least one maytansinoid ligand (e.g. maytansinoid DM1 or DM4). It has been found that maytansinoids are sensitive to a reducing environment. For example, maytansinoid DM1 forms several reaction products when treated with sodium borohydride. Therefore, advantageously, a meta-stable nanoparticle may be formed using the process of the present invention and a first ligand species that is stable in a reducing environment (e.g. glucose-C2-thiol). Once the meta-stable nanoparticle has been formed, an excess of the reducing agent-sensitive ligand (e.g. maytansinoid DM1 or maytansinoid DM4) is added to the solution comprising the meta-stable nanoparticles. The reducing agent-sensitive ligand (e.g. maytansinoid DM1 or maytansinoid DM4) then populates uncapped sites on the surface of the core of the nanoparticle to form stable nanoparticles having a mixed corona (in this example, a mixture of glucose-C2 ligands and maytansinoid DM1 or maytansinoid DM4 ligands).

In some cases, the further ligands are added in excess, optionally stoichiometric excess, relative to the amount of said at least one species of ligand in said first liquid.

In certain cases, at least a portion of the further ligands react with the nanoparticles and thereby become covalently bound to the core of the nanoparticle.

In some cases in accordance with the first aspect of the present invention, the process further comprises collecting the nanoparticles by separating the nanoparticles from the second liquid. The nanoparticles may be subjected to one or more post-production treatment steps selected from the group consisting of: dialyzing, washing, drying, centrifugation (e.g. ultracentrifugation) and sterilizing.

In some cases, the process of the first aspect of the present invention further comprises bringing the nanoparticles into contact with at least one species of peptide, whereby the at least one species of peptide non-covalently binds to the corona of the nanoparticles to form peptide-bound nanoparticles. This may be accomplished by, for example, mixing a solution (e.g. an aqueous solution) comprising the nanoparticles with a solution (e.g. an aqueous solution) comprising the at least one species of peptide and for a time and at a temperature that permits the peptide molecules to bind non-covalently (e.g. electrostatically) to the corona of the nanoparticle. Suitable peptides include therapeutically active agents such as: insulin, GLP-1, exenatide, amylin, octreotide, teriparatide, a cytokine and an antibody (see also, e.g., WO2011/154711).

In some cases, the process of the first aspect of the present invention further comprises formulating or packaging the nanoparticles into a pharmaceutical composition or delivery form. In particular, the nanoparticles formed by the process of the present invention may be combined with one or more pharmaceutically acceptable carriers, excipients or diluents.

In certain cases the pharmaceutical composition may be formulated for delivery via an injectable route. In some cases the nanoparticles may be incorporated into a polymeric film, e.g. for transbuccal delivery.

The present invention includes the combination of the aspects and preferred features described except where such a combination is clearly impermissible or is stated to be expressly avoided. These and further aspects and embodiments of the invention are described in further detail below and with reference to the accompanying examples and figures.

BRIEF DESCRIPTION OF THE FIGURES

FIG. 1 shows a schematic depiction of an embodiment of the present invention. A solution comprising gold salt ($Au^{3+}$) and ligands is added dropwise to a vessel containing an excess of reducing agent ($BH_4^-$). As $Au^{3+}$ is added dropwise it meets an excess of $BH_4^-$, hence all gold atoms in the droplet should be reduced to completion (without the need for mixing). Providing ligands are available at a suitable concentration, nanoparticles are produced.

FIG. 5 shows a schematic illustration of a continuous reductant flow embodiment of the method of the present invention. A horizontal jet of a solution containing sodium borohydride is shown from left to right. A solution of gold salt ($Au^{3+}$) and ligands is ejected from the piezoelectric droplet generator to form a downward stream of droplets passing through air before making contact with the jet containing sodium borohydride. Reduction of the gold salt and formation of gold nanoparticles with a corona of ligands occurs rapidly, and the jet stream of liquid, now containing formed nanoparticles, enters an elbow joint section of tubing (shown at the right-hand end of the jet) and is directed downwards to a collecting vessel.

DETAILED DESCRIPTION OF THE INVENTION

In describing the present invention, the following terms will be employed, and are intended to be defined as indicated below.

Nanoparticles

As used herein, "nanoparticle" refers to a particle having a nanomeric scale, and is not intended to convey any specific shape limitation. In particular, "nanoparticle" encompasses nanospheres, nanotubes, nanoboxes, nanoclusters, nanorods and the like. In certain embodiments the nanoparticles and/or nanoparticle cores contemplated herein have a generally polyhedral or spherical geometry.

Nanoparticles comprising a plurality of carbohydrate-containing ligands have been described in, for example, WO 2002/032404, WO 2004/108165, WO 2005/116226, WO 2006/037979, WO 2007/015105, WO 2007/122388, WO 2005/091704 (the entire contents of each of which is expressly incorporated herein by reference) and such nanoparticles may find use in accordance with the present invention.

As used herein, "corona" refers to a layer or coating, which may partially or completely cover the exposed surface of the nanoparticle core. The corona includes a plurality of ligands which generally include at least one carbohydrate moiety, one surfactant moiety and/or one glutathione moiety. Thus, the corona may be considered to be an organic layer that surrounds or partially surrounds the metallic core. In certain embodiments the corona provides and/or participates in passivating the core of the nanoparticle. Thus, in certain cases the corona may include a sufficiently complete coating layer substantially to stabilise the semiconductor or metal-containing core. However, it is specifically contemplated herein that certain nanoparticles having cores, e.g., that include a metal oxide-containing inner core coated with a noble metal may include a corona that only partially coats the core surface. In certain cases the corona facilitates solubility, such as water solubility, of the nanoparticles of the present invention.

Nanoparticles are small particles, e.g. clusters of metal or semiconductor atoms, that can be used as a substrate for immobilising ligands.

Preferably, the nanoparticles have cores having mean diameters between 0.5 and 50 nm, more preferably between 0.5 and 10 nm, more preferably between 0.5 and 5 nm, more preferably between 0.5 and 3 nm and still more preferably between 0.5 and 2.5 nm. When the ligands are considered in addition to the cores, preferably the overall mean diameter of the particles is between 2.0 and 20 nm, more preferably between 3 and 10 nm and most preferably between 4 and 5 nm. The mean diameter can be measured using techniques well known in the art such as transmission electron microscopy.

The core material can be a metal or semiconductor (said semiconductor optionally comprising metal atoms or being an organic semiconductor) and may be formed of more than one type of atom. Preferably, the core material is a metal selected from Au, Fe or Cu. Nanoparticle cores may also be formed from alloys including Au/Fe, Au/Cu, Au/Gd, Au/Fe/Cu, Au/Fe/Gd and Au/Fe/Cu/Gd, and may be used in the present invention. Preferred core materials are Au and Fe, with the most preferred material being Au. The cores of the nanoparticles preferably comprise between about 100 and 500 atoms (e.g. gold atoms) to provide core diameters in the nanometre range. Other particularly useful core materials are doped with one or more atoms that are NMR active, allowing the nanoparticles to be detected using NMR, both in vitro and in vivo. Examples of NMR active atoms include $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$, and lanthanides$^{+3}$, or quantum dots.

Nanoparticle cores comprising semiconductor compounds can be detected as nanometre scale semiconductor crystals are capable of acting as quantum dots, that is they can absorb light thereby exciting electrons in the materials to higher energy levels, subsequently releasing photons of light at frequencies characteristic of the material. An example of a semiconductor core material is cadmium selenide, cadmium sulphide, cadmium tellurium. Also included are the zinc compounds such as zinc sulphide.

In some embodiments, the nanoparticle or its ligand comprises a detectable label. The label may be an element of the core of the nanoparticle or the ligand. The label may be detectable because of an intrinsic property of that element of the nanoparticle or by being linked, conjugated or associated with a further moiety that is detectable. Preferred examples of labels include a label which is a fluorescent group, a radionuclide, a magnetic label or a dye. Fluorescent groups include fluorescein, rhodamine or tetramethyl rhodamine, Texas-Red, Cy3, Cy5, etc., and may be detected by excitation of the fluorescent label and detection of the emitted light using Raman scattering spectroscopy (Y. C. Cao, R. Jin, C. A. Mirkin, Science 2002, 297: 1536-1539). In some cases, the detectable label may comprise fluorescein isothiocyanate (FITC). In certain cases, the detectable label (e.g. FITC) may be covalently linked to the core of the nanoparticle, e.g. via a linker.

In some embodiments, the nanoparticles may comprise a radionuclide for use in detecting the nanoparticle using the radioactivity emitted by the radionuclide, e.g. by using PET, SPECT, or for therapy, i.e. for killing target cells. Examples of radionuclides commonly used in the art that could be readily adapted for use in the present invention include $^{99m}Tc$, which exists in a variety of oxidation states although the most stable is $TcO^{4-}$; $^{32}P$ or $^{33}P$; $^{57}Co$; $^{59}Fe$; $^{67}Cu$ which is often used as $Cu^{2+}$ salts; $^{67}Ga$ which is commonly used a $Ga^{3+}$ salt, e.g. gallium citrate; $^{68}Ge$; $^{82}Sr$; $^{99}Mo$; $^{103}Pd$; $^{111}In$ which is generally used as $In^{3+}$ salts; $^{125}I$ or $^{131}I$ which is generally used as sodium iodide; $^{137}Cs$; $^{153}Gd$; $^{153}Sm$; $^{158}Au$; $^{186}Re$; $^{201}Tl$ generally used as a $Tl^+$ salt such as thallium chloride; $^{39}Y^{3+}$; $^{71}Lu^{3+}$; and $^{24}Cr^{2+}$. The general use of radionuclides as labels and tracers is well known in the art and could readily be adapted by the skilled person for use in the aspects of the present invention. The radionuclides may be employed most easily by doping the cores of the nanoparticles or including them as labels present as part of ligands immobilised on the nanoparticles.

Actives

As used herein the term "bioaffecting agent" is intended to encompass drugs and pro-drugs that exert an effect on a biological system, preferably a therapeutic effect. Class of active agent contemplated herein include small molecule organic compounds, peptides, polypeptides and nucleic acids. Particular examples include: chemotherapeutic agents (e.g. temozolomide, irinotecan, chlorotoxin, carmustine, platinum(IV), platinum(II), camptothecin, doxorubicin, docetaxel Maytansine, Maytansinoids (e.g. DM1 and DM4), monomethyl auristatin E (MMAE) and/or histone deacetylase (HDAC) inhibitors such as Panobinostat, Vorinostat, Romidepsin and Chidamide); peptides or polypeptides (e.g. insulin, GLP-1, amylin, exenatide, octreotide, teriparatide, glucagon, a cytokine, and/or an antibody); DNA or RNA (including, e.g. siRNA).

The following is presented by way of example and is not to be construed as a limitation to the scope of the claims.

EXAMPLE

Example 1—Piezoelectric Ejection-Based Synthesis of Gold Nanoparticles

A solution containing $HAuCl_4$ ($[Au^{3+}]$ of 1 mg/ml), glucose-C2-disulphide ($Au^{3+}$: Glucose-C2-disulphide 1:3 mole ratio) in DMSO was ejected from a single piezoelectric droplet generator using the following ejection conditions: 44V, 13 µs pulse, 50° C., n=4000 Hz. The droplets were ejected into a 12 mL vial containing 8 mL of an aqueous solution of $NaBH_4$ at a concentration of 0.05M.

The resulting nanoparticles were isolated by Amicon ultracentrifugation after droplet ejection was complete. Meta-stable nanoparticles of appropriate size were produced (demonstrated by a very small plasmon band). It was found that these nanoparticles "ripened" overnight with the size increasing to a diameter of >8 nm (red colour observed). The present inventors believe that this indicates that the gold nanoparticle core was not fully capped with ligand at the point when the nanoparticles were isolated (i.e. the nanoparticles were initially meta-stable).

A further batch of gold nanoparticles was then produced using the above-described reactant concentrations and droplet ejection conditions. After ejection was complete (20 minutes), a further 3× mole equivalents of Glucose C2 disulfide was added to the solution containing the nanoparticles. The mixture was stirred for 1 hour.

Figure 1:
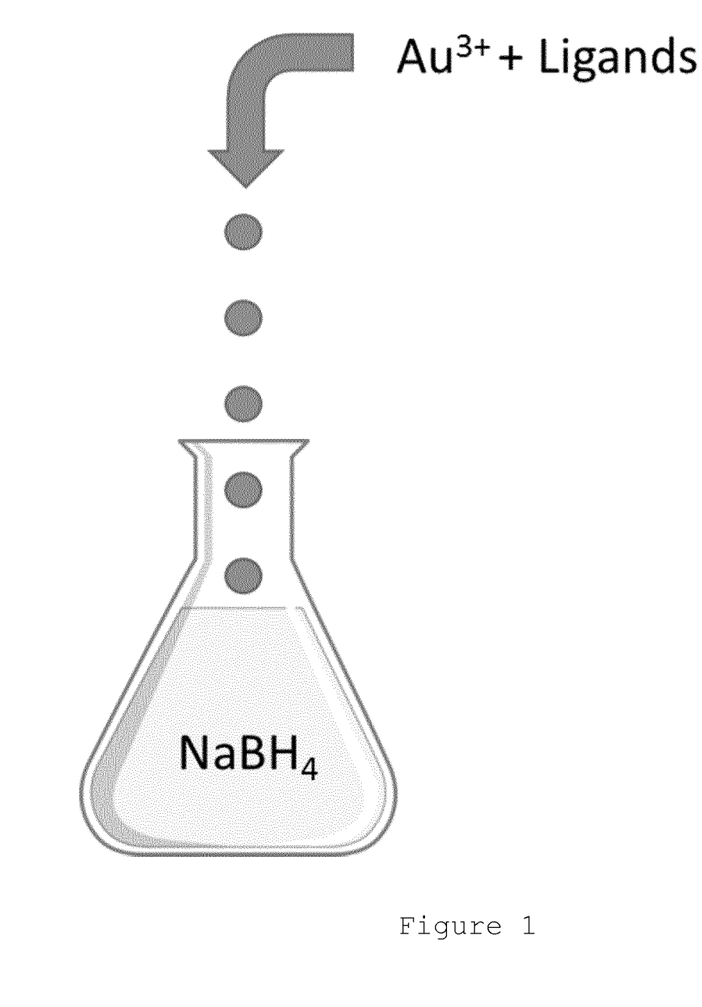
Figure 2:
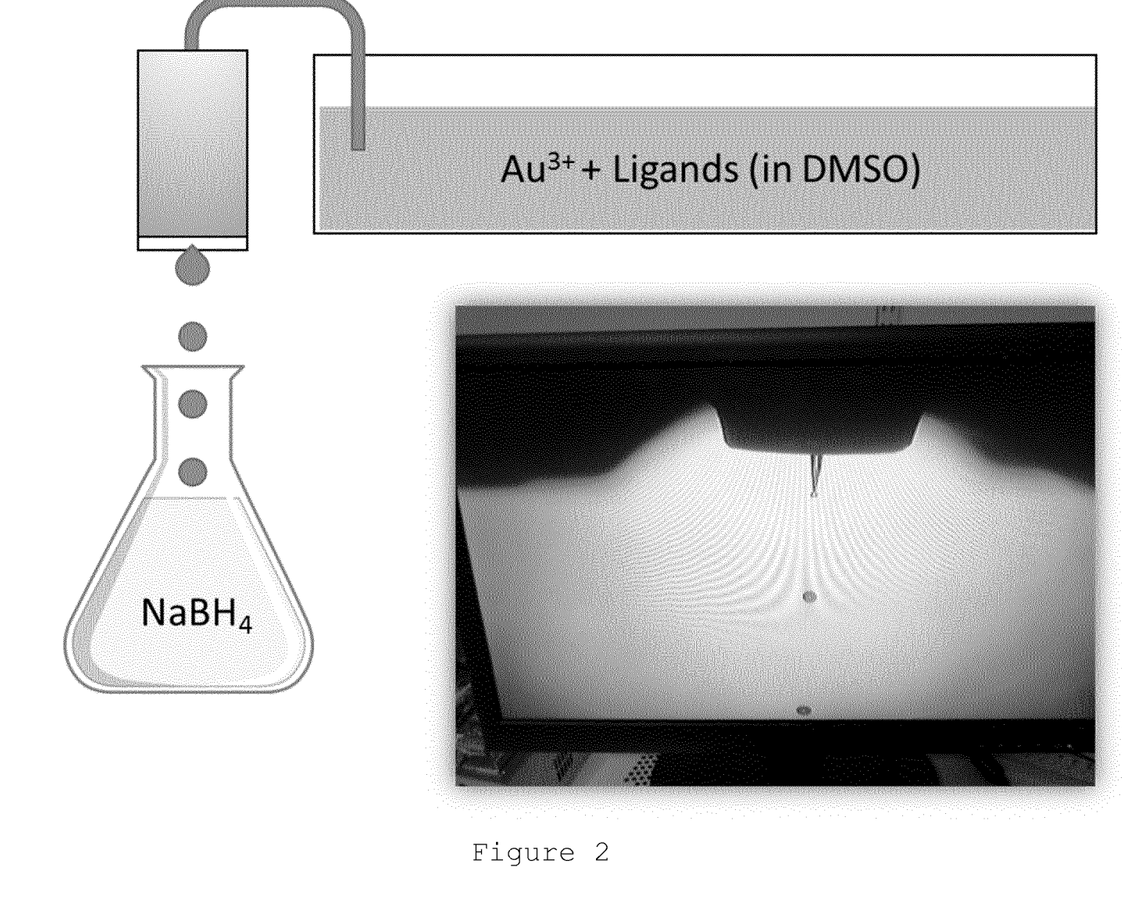
FIG. 2 shows a schematic depiction of an embodiment of the present invention employing a piezoelectric droplet generator. The insert panel shows a high-speed photograph of the droplets ejected from the orifice of the piezoelectric droplet generator. A solution of $Au^{3+}$ and Glucose-C2 dimer (2'-thioethyl-β-D-glucopyranoside provided as a disulphide dimer) in DMSO was ejected from the piezoelectric droplet generator as a stable stream of droplets (ejection conditions: 44V, 13 μs pulse, 50° C., v=4000 Hz) into a solution containing $NaBH_4$.
Figure 3:
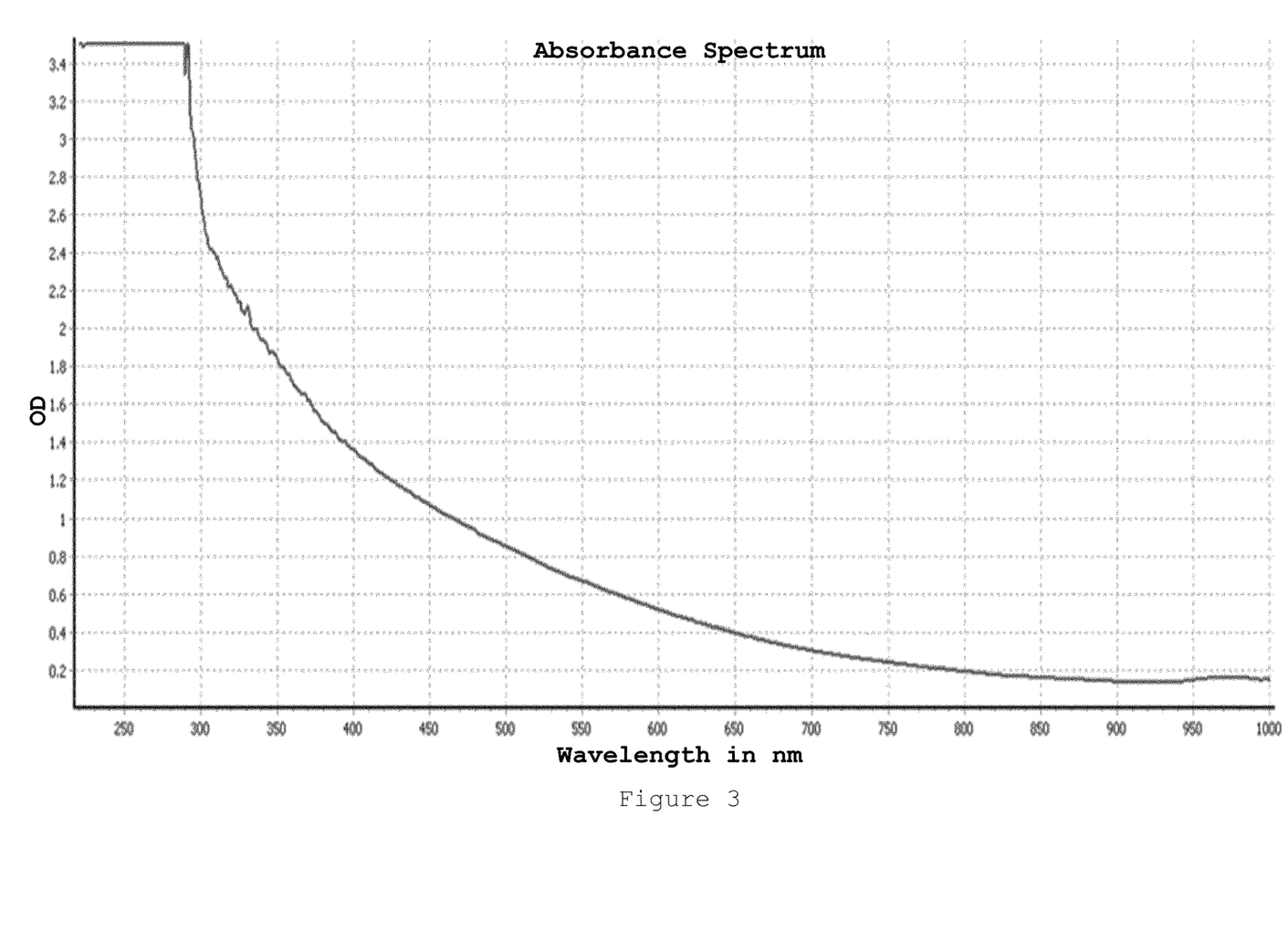
FIG. 3 shows the absorbance spectrum of gold nanoparticles having a corona of glucose-C2 ligands, produced by the method of the present invention. Optical density (y-axis) is plotted against wavelength in nm (x-axis). The absorbance spectrum shows little or no evidence of a surface plasmon resonance band.
Figure 4:
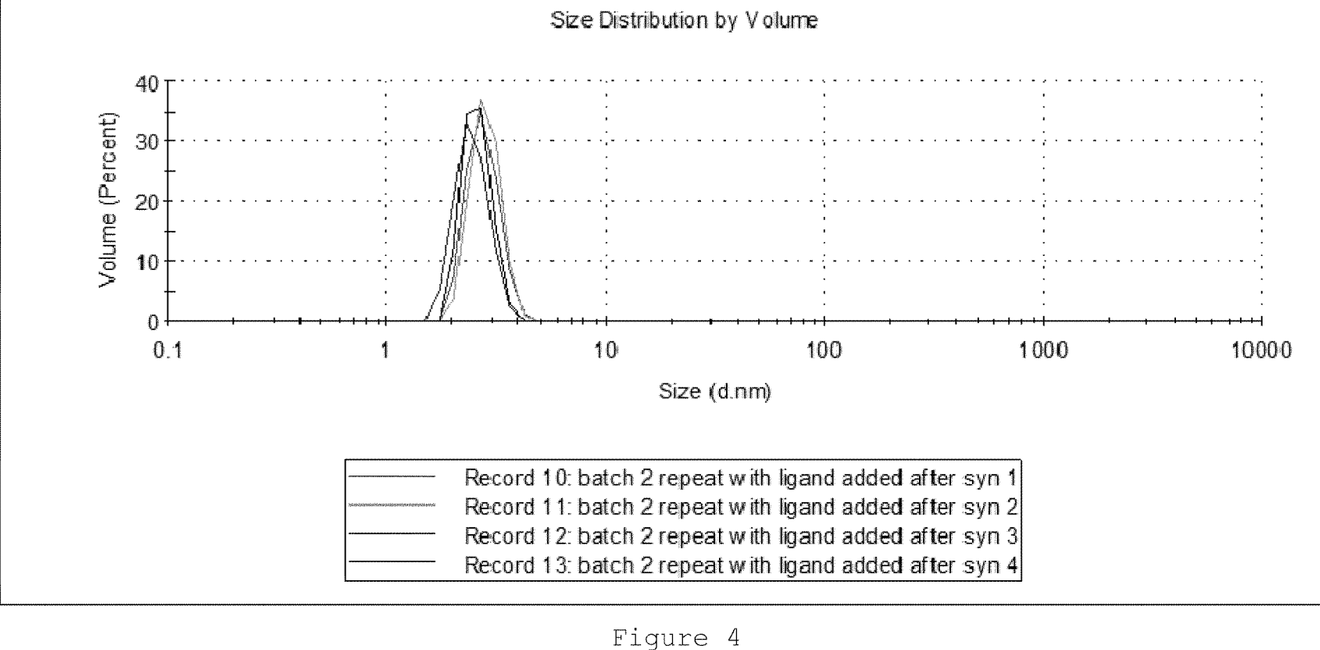
FIG. 4 shows four size distribution traces determined by dynamic light scattering (DLS), in which the percentage (y-axis) by volume of nanoparticles in the population are plotted against the nanoparticle diameter in nm (x-axis). The average diameter was found to be 2.7 nm. The nanoparticles for each of the four traces were produced by a method embodiment of the present invention in which excess (3× mole equivalent) of glucose-C2 disulphide was added to the solution containing the nanoparticles after droplet ejection was complete (20 minutes) and the resulting mixture stirred for 1 hour.
Figure 5:
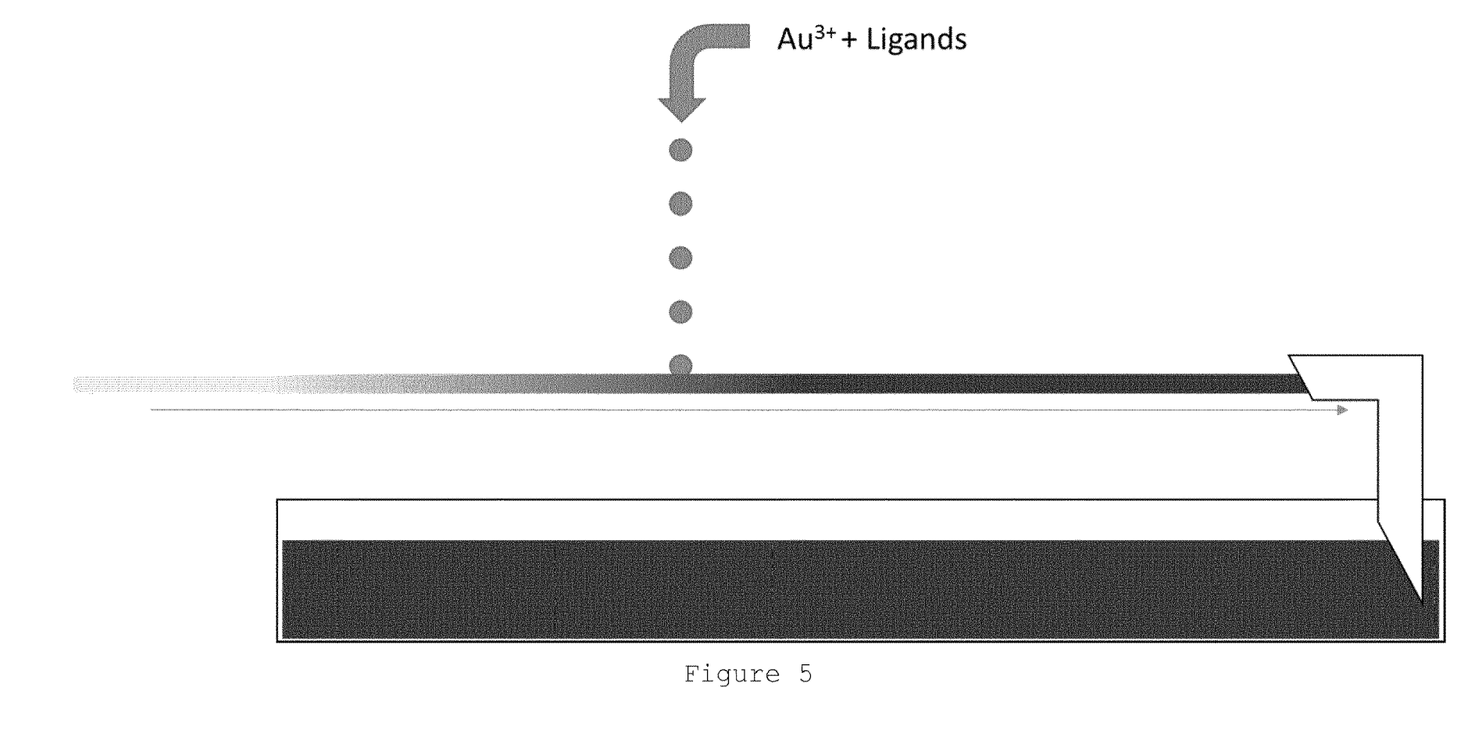
Figure 6:
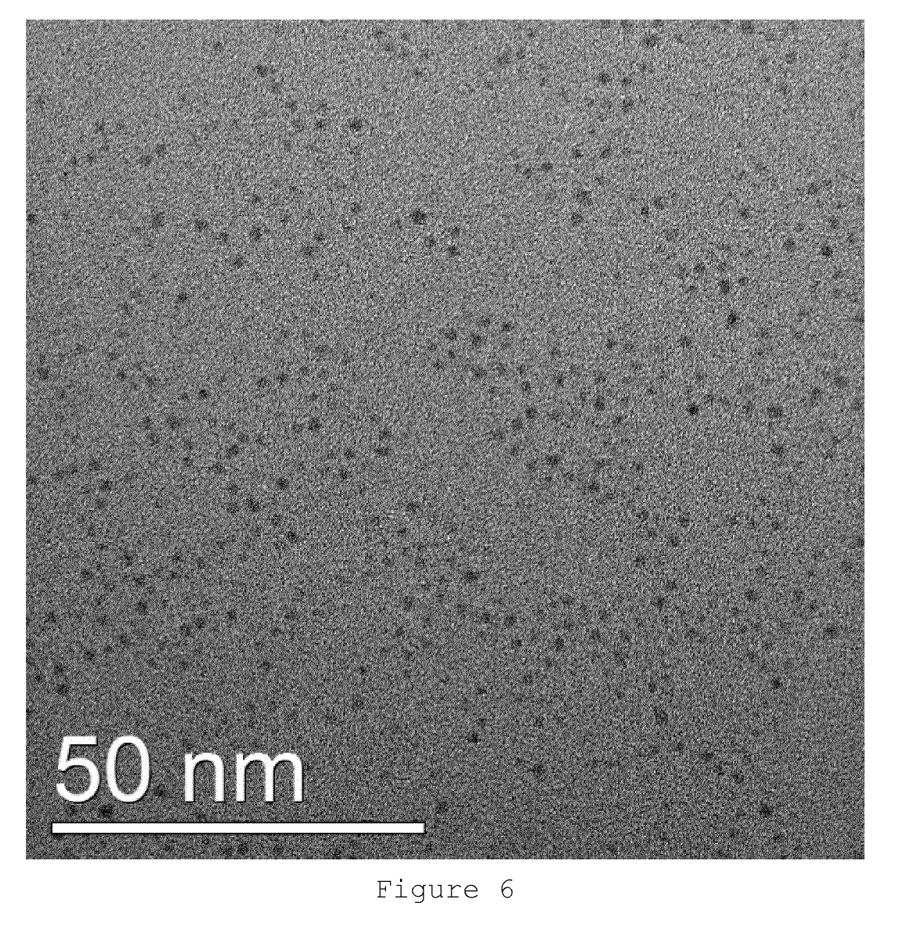
FIG. 6 shows a transmission electron microscopy (TEM) image of nanoparticles produced according the process of the present invention. A 50 nm scale bar is shown. The dark spots show generally spherical gold-core nanoparticles. The batch of nanoparticles were produced via the piezoelectric droplet generator that ejected droplets of a solution of $Au^{3+}$ and Glucose-C2 dimer in DMSO into a solution containing $NaBH_4$.

Stable nanoparticles produced of appropriate size (average diameter of 2.7 nm by dynamic light scattering (DLS)—see FIGS. 3 and 4. These were visualised by transmission electron microscopy—see FIG. 6.

Further experiments were then carried out to investigate the scalability of the process. In particular, increasing $Au^{3+}$ and ligand concentration in the first liquid increases $Au_{(s)}$ yield per unit time. It was found that $Au^{3+}$ concentrations of 5 mg/mL, 10 mg/mL, 25 mg/mL and 30 mg/mL (and correspondingly increased ligand concentrations to maintain a 1:3 Au:ligand ratio) produced stable gold nanoparticles with essentially no plasmon resonance band observable. The following calculation provides an estimated yield achievable using a 512 nozzle print-head array at 4 kHz droplet generation frequency:

$$4000 \text{ Hz} \times 512 \text{ nozzles} = 2.05 \text{ MHz}$$

$$\text{Droplet volume} = 42 pL$$

$$= 0.086 \text{ mL/s}$$

$$= 5.16 \text{ mL/min}$$

$$= 309 \text{ mL/hr}$$

At $[Au^{3+}]$=30 mg/mL (and assuming ~90% yield), this would give 8.34 g $Au_{(s)}$/hr.

It should be noted however, that the above calculation provides representative figures and should not be taken as a maximum yield for the process of the present invention.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A process for producing nanoparticles, comprising:
providing a first liquid comprising a metal salt and at least one species of ligand having a functional group capable of binding to a metal surface,
providing a second liquid comprising a reducing agent, wherein the second liquid is provided as a jet passing through a gas and wherein the jet of second liquid is not in contact with any wall or channel for at least part of its length;
providing at least one liquid droplet generator operable to generate liquid droplets, said at least one liquid droplet generator comprising a piezoelectric component,
causing the at least one liquid droplet generator to form liquid droplets of the first liquid,
passing the liquid droplets through the gas to contact the second liquid so as to cause the metal salt and the at least one species of ligand to come into contact with the reducing agent, thereby causing self-assembly of nanoparticles, said nanoparticles having a core of said metal and a corona comprising a plurality of said ligands covalently bound to the core.

2. The process according to claim 1, wherein the metal salt comprises a salt of Au, Ag, Cu, Pt, Pd, Fe, Co, Gd, Eu, or Zn.

3. The process according to claim 2, wherein the metal salt comprises $HAuCl_4$.

4. The process according to claim 1, wherein the at least one species of ligand comprises a carbohydrate moiety and wherein the carbohydrate moiety comprises glucose, galactose, glucosamine, N-acetylglucosamine, mannose, fucose and/or lactose, or a glycoside thereof.

5. The process according to claim 1, wherein the at least one species of ligand comprises an oligo ethylene glycol or a polyethylene glycol.

6. The process according to claim 1, wherein the at least one species of ligand comprises a therapeutic or bioaffecting agent.

7. The process according to claim 6, wherein the at least one species of ligand comprises a compound selected from the group consisting of: doxorubicin, irinotecan, platinum (II), platinum (IV), temozolomide, chlorotoxin, carmustine, camptothecin, docetaxel, sorafenib, maytansine, a maytansinoid (e.g. maytansinoid DM1 or maytansinoid DM4), monomethyl auristatin E (MMAE) and a histone deacetylase (HDAC) inhibitor.

8. The process according to claim 1, wherein the droplet generators operate in drop-on-demand mode.

9. The process according to claim 1, wherein a signal generator supplies an electric field to the piezoelectric component.

10. The process according to claim 1, wherein the frequency of liquid droplet generation per liquid droplet generator outlet is in the range 0.1 to 100 kHz.

11. The process according to claim 1, wherein said liquid droplets have an individual droplet volume in the range 1 to 100 pL.

12. The process according to claim 1, wherein the process is for forming meta-stable nanoparticles.

13. The process according to claim 1, wherein the process further comprises a step of adding further ligands to a solution comprising the nanoparticles and wherein the further ligands are different from said at least one species of ligand in the first liquid.

14. The process according to claim 1, further comprising collecting the nanoparticles by separating the nanoparticles from the second liquid.

15. The process according to claim 14, further comprising formulating or packaging the nanoparticles into a pharmaceutical composition or delivery form.

* * * * *

UNITED STATES PATENT AND TRADEMARK OFFICE
CERTIFICATE OF CORRECTION

| | |
|---|---|
| PATENT NO. | : 11,090,626 B2 |
| APPLICATION NO. | : 16/077703 |
| DATED | : August 17, 2021 |
| INVENTOR(S) | : Palmer et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 99 days.

Signed and Sealed this
Eighth Day of November, 2022

*Katherine Kelly Vidal*
Katherine Kelly Vidal
*Director of the United States Patent and Trademark Office*